(12) United States Patent
Pickens

(10) Patent No.: US 7,923,036 B2
(45) Date of Patent: Apr. 12, 2011

(54) HALOGEN-CONTAINING SANITIZING COMPOSITION

(75) Inventor: Stanley R. Pickens, Monroeville, PA (US)

(73) Assignee: PPG Industries Ohio, Inc., Cleveland, OH (US)

( * ) Notice: Subject to any disclaimer, the term of this patent is extended or adjusted under 35 U.S.C. 154(b) by 402 days.

(21) Appl. No.: 12/241,216

(22) Filed: Sep. 30, 2008

(65) Prior Publication Data

US 2010/0080857 A1    Apr. 1, 2010

(51) Int. Cl.
| | |
|---|---|
| A01N 59/14 | (2006.01) |
| A01N 59/08 | (2006.01) |
| A01N 59/00 | (2006.01) |
| A01N 43/66 | (2006.01) |
| A01N 43/76 | (2006.01) |
| A01N 43/50 | (2006.01) |
| A61K 33/22 | (2006.01) |
| A61K 33/14 | (2006.01) |
| A61K 33/00 | (2006.01) |
| A61K 31/53 | (2006.01) |
| A61K 31/42 | (2006.01) |
| A61K 31/415 | (2006.01) |

(52) U.S. Cl. ........ 424/659; 424/661; 424/665; 424/722; 514/241; 514/376; 514/389; 514/401

(58) Field of Classification Search .................. None
See application file for complete search history.

(56) References Cited

U.S. PATENT DOCUMENTS

| | | |
|---|---|---|
| 3,325,411 A | 6/1967 | Stepanek |
| 3,474,037 A | 10/1969 | Goldsmith et al. |
| 3,793,216 A | 2/1974 | Dychdala |
| 3,969,546 A | 7/1976 | Saeman |
| 4,594,091 A | 6/1986 | Girvan |
| 5,478,482 A | 12/1995 | Jones et al. |
| 5,514,287 A | 5/1996 | Jones et al. |
| 5,676,844 A | 10/1997 | Girvan |
| 6,022,480 A | 2/2000 | Girvan et al. |
| 6,776,926 B2 | 8/2004 | Martin |
| 2004/0040915 A1 | 3/2004 | Connelly |
| 2004/0082491 A1 | 4/2004 | Olson et al. |

FOREIGN PATENT DOCUMENTS

| | | | |
|---|---|---|---|
| EP | 0875558 A2 | | 11/1998 |
| JP | 02251552 | * | 10/1990 |
| JP | 02252743 | * | 10/1990 |
| RO | 113234 | * | 5/1998 |
| WO | WO-9636224 | * | 11/1996 |
| WO | WO 99/61376 | | 12/1999 |
| WO | WO 2004/089081 A2 | | 10/2004 |

* cited by examiner

Primary Examiner — Johann R Richter
Assistant Examiner — Jessica Kassa
(74) Attorney, Agent, or Firm — Irwin M. Stein

(57) ABSTRACT

Compositions comprising a mixture of (a) a major amount of solid halogen-containing sanitizer material and (b) a minor amount of calcium oxide modified particulate boric acid, the amount of calcium oxide modified particulate boric acid being sufficient to enable the composition to be classified as a class 1 or class 2 NFPA oxidizer are described. Also described is particulate boric acid at least a portion of the particles thereof having on their surface at least a partial coating of calcium oxide, and a method for preparing such coated particulate boric acid.

11 Claims, No Drawings

HALOGEN-CONTAINING SANITIZING COMPOSITION

FIELD OF THE INVENTION

This invention relates to compositions for the treatment of water systems to control microbial growth. In particular, this invention relates to compositions comprising a solid halogen-containing material that sanitize and/or disinfect water systems and surfaces that require sanitizing.

BACKGROUND OF THE INVENTION

Recreational and commercial water systems, as well as natural bodies of water, e.g., ponds, are subject to contamination from the presence and growth of microbes, e.g., algae, pathogenic bacteria and fungi. The sanitization of standing or recirculating water systems typically involves introducing a halogen or halogen-containing material, e.g., a hypohalite material, such as a hypochlorite or hypobromite material, into the water system so as to establish a desired level, e.g., a sanitizing amount, of free available halogen ("FAHal"), e.g., free available chlorine ("FAC"), within the water system. The presence of free available halogen serves to eradicate or control deleterious amounts of microbial species, e.g., pathogenic bacteria, algae, fungi, etc that are present in the water comprising the water system. Hypochlorous acid and hypobromous acid are oxidizing materials that can also remove nutrients from water to which they are added, thus providing indirect protection against microbial infestation. Sanitation of water contacted by humans and animals is required because exposure to unsanitized or inadequately sanitized water that contains deleterious amounts of pathogenic bacteria, viruses, protozoa, etc can lead to the development of infection or disease.

FAHal, e.g., FAC or bromine, can be established in an aqueous system by adding regularly a source of hypohalous acid, e.g., hypochlorous acid (HOCl) or hypochlorite anion (ClO$^-$), or hypobromous acid (HOBr) or hypobromous anion (BrO$^-$) to the water comprising the aqueous system. There are many hypohalite generating materials. Non-limiting examples of hypohalite generating materials include chlorine gas, alkali metal hypochlorites, e.g., sodium hypochlorite and lithium hypochlorite, alkaline earth metal hypochlorites, e.g., calcium hypochlorite, halogenated hydantoins, such as the chlorinated and brominated hydantoins, e.g., 1,3-dibromo-5,5-dimethylhydantoin, chlorinated isocyanuric acid and its alkali metal derivatives, such as trichloroisocyanuric acid (also known as tri-chloro-s-triazinetrione), dichloroisocyanuric acid, and the corresponding salts sodium and potassium dichloro-s-triazinetrione, the N-halo-2-oxazolidinones, such as 3-chloro-4,4-dimethyl-2-oxazolidinone, and N,N'-dihalo-2-imidazolidinones, such as 1,3-dichloro-4,4,5,5-tetramethyl-2-imidazolidinone.

Recreational bodies of water, e.g., swimming pools, hot tubs, spas, etc, typically are treated so as to contain a level of FAHal, e.g., FAC, of from 1 to 10, e.g., 1 to 4, parts per million parts of water (ppm), sometimes reported as milligrams per Liter (mg/L). FAC levels in recreational bodies of water are generally maintained at from 1 to 2 ppm. FAC levels of 1 ppm or less, e.g., 0.5 to 1 ppm, are commonly maintained in cooling water systems. Water having a FAHal, e.g., FAC, content in amounts of greater than 10 ppm (generally in the range of hundreds to thousands of mg/L) can be used to sanitize surfaces or articles to which it is applied, e.g., food, equipment and tables used for the processing of raw food or in the preparation of processed food products.

Hypohalous acid, e.g., hypochlorous acid, or hypohalite anion, e.g., hypochlorite anion, can be introduced into water systems by passing the water, or a portion thereof, through a container that contains a donor source of the hypohalous acid or hypohalite anion. Other means include introducing chlorine directly into the water or adding the hypohalous acid donor material directly to the body of water to be treated. A common donor source of hypochlorous acid or hypochlorite anion is calcium hypochlorite. Calcium hypochlorite, e.g., granular calcium hypochlorite, can be added directly to the water to be treated, or placed in a container in the form of granules or tablets. When water is brought into contact with the calcium hypochlorite in the container, the calcium hypochlorite dissolves, thereby forming an aqueous solution comprising hypochlorite anion. This solution may be mixed with a water supply, added to water to be sanitized, or used directly for the intended application.

In the case of a standing or recirculating body of water, e.g., swimming pools, periodic batch additions of higher levels of hypochlorite anion can be made to the body of water in addition to the relatively steady and lower level additions described previously. Such batch additions of higher levels of hypochlorite anion are commonly referred to as a "shock treatment" or as "super chlorination" and are made on a periodic basis, e.g., once a week or once a month. Typically, the purpose of a shock treatment is to briefly increase the FAC of the body of water, e.g., by 5 to 10 parts per million (ppm), to consume accumulated organic material, destroy chloramines and/or control algae blooms. A shock treatment is administered by, for example, preparing a concentrated aqueous solution of calcium hypochlorite and adding this concentrated solution to the body of water, or distributing, e.g., broadcasting, granulated calcium hypochlorite directly over the surface of the body of water.

Use of boron derivatives, such as boric acid, sodium borates and potassium borates for inhibiting algal and fungal growth in recreational water systems, e.g., swimming pools, has been described. In addition, such compounds can serve as a pH buffer in the water. However, when boric acid is blended with solid calcium hypochlorite, e.g., granular calcium hypochlorite, the calcium hypochlorite assay, e.g., the FAC content of the calcium hypochlorite, in the resultant blend diminishes faster over time than an equivalent amount of the calcium hypochlorite used to prepare the blend that is substantially free of boric acid. Use of a low assay calcium hypochlorite can result in inadequate sanitization of water to which it is added. Therefore, it is desirable to provide a calcium hypochlorite-boric acid composition that is more stable, vis-à-vis, the loss of FAC assay, i.e., the composition has an improved shelf life.

Calcium hypochlorite is a material that can cause or enhance the combustion of organic materials by providing oxygen for combustion, e.g., it serves as an oxidizer. In accordance with US Department of Transportation (DOT) regulations; namely, Title 49, Code of Federal Regulations (CFR), part 173, section 127, paragraph (a), subparagraph (1), [49 CFR §173.127(a)(1)], calcium hypochlorite is categorized as a Division 5.1 oxidizer. More particularly, it is classified as a Packing Group II oxidizer material [49 CFR §173.127(b)(ii)]. The transport of a material categorized as a Division 5.1 oxidizer requires the use of special precautions, which can include the use of special containers.

Further, the National Fire Protection Association (NFPA) classifies calcium hypochlorite having greater than 50 percent FAC as a Class 3 oxidizer. NFPA Class 3 oxidizers may require separate free standing storage facilities and/or special sprinkler systems. Such special storage and handling requirements imposes increased costs on the use of calcium hypochlorite, particularly when the amount of calcium hypochlorite that is required to be stored on site is large.

Boric acid has been described as an exotherm control agent for peroxyacid compounds used in detergent compositions. However, as noted, when boric acid is blended with solid calcium hypochlorite, it tends to destabilize the calcium hypochlorite. Hence, blending boric acid with calcium hypochlorite would be counterproductive because it would lower the shelf life of the calcium hypochlorite, and perhaps even precipitate a runaway thermal decomposition, though mitigating the amount of heat released as a result of the thermal decomposition.

It would be advantageous to have solid halogen-containing compositions, e.g., calcium hypochlorite compositions that are not classified as a Packing Group I or Packing Group II Division 5.1 oxidizer, but are classified as a Packing Group III Division 5.1 oxidizer or as a non-Division 5.1 oxidizer. In the NFPA system, it would be advantageous to have solid halogen-containing compositions, such as calcium hypochlorite compositions, that are not classified as a Class 4 or Class 3 NFPA oxidizer, but are classified as a Class 1 or Class 2 NFPA oxidizer. Further, it would be advantageous that calcium hypochlorite compositions that contain boric acid do not lose FAC assay over time at a rate greater than an equivalent calcium hypochlorite composition that does not contain boric acid. It is also desirable that a solid calcium hypochlorite composition has an FAC assay that is at least sufficient to allow its use in the batch and/or continuous sanitization of water systems, e.g., a standing or recirculating water system such as a body of water, swimming pool, spa, hot tub, cooling tower, evaporative condenser, etc.

SUMMARY OF THE INVENTION

The present invention is directed to a composition, comprising a mixture of (a) a major amount of solid halogen-containing sanitizing material and (b) a minor amount of calcium oxide-modified particulate boric acid, the amount of calcium oxide-modified boric acid being sufficient to enable the composition to be classified as a class 1 or class 2 NFPA oxidizer.

Additionally, the present invention provides particulate boric acid having at least a partial coating of calcium oxide. The present invention also provides a method for preparing particulate boric acid having at least a partial coating of calcium oxide comprising blending particulate boric acid and finely-divided calcium oxide, and heating the resulting blend at a temperature sufficient to cause the calcium oxide to adhere to the surface of the particulate boric acid.

DETAILED DESCRIPTION OF THE INVENTION

For purposes of this specification (other than in the operating examples), unless otherwise indicated, all numbers expressing quantities and ranges of materials, process conditions, etc are to be understood as modified in all instances by the term "about". Accordingly, unless indicated to the contrary, the numerical parameters set forth in this description and attached claims are approximations that can vary depending upon the desired results sought to be obtained by the present invention. At the very least and not as an attempt to limit the application of the doctrine of equivalents to the scope of the attached claims, each numerical parameter should at least be construed in light of the number of reported significant digits and by applying ordinary rounding techniques. Further, as used in this description and the attached claims, the singular forms "a", "an" and "the" are intended to include plural referents, unless expressly and unequivocally limited to one referent.

Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in its respective testing measurement, including that found in the measuring instrument. Also, it is to be understood that any numerical range recited herein is intended to include all sub-ranges subsumed therein. For example, a range of "1 to 10" is intended to include all sub-ranges between and including the recited minimum value of 1 and the recited maximum value of 10; i.e., a range having a minimum value equal to or greater than 1 and a maximum value of equal to or less than 10. Because the disclosed ranges are continuous, they include every value between the minimum and maximum values. Unless expressly indicated otherwise, the various numerical ranges specified in this application are approximations.

As used in the following description and claims, the following terms have the indicated meanings:

The term "calcium oxide-modified boric acid" means particulate boric acid, at least a portion of which has calcium oxide adhering to or coating the surface of said particles. The amount of calcium oxide adhering to or coating the surface of the particulate boric acid may vary. For purposes of exemplification only, calcium oxide may be present on from 20 percent or less to 100 percent of the surface of the particles of boric oxide. In another example, calcium oxide may be present on from 25 to 75 percent of the surface of the particles of boric acid. The portion of the particulate boric acid to which calcium oxide is adhered (or which is coated with calcium oxide) will be sufficient so that when a chosen amount of such a calcium oxide modified boric acid material is admixed with particulate halogen-containing sanitizing material, such as calcium hypochlorite, the resulting mixture will have an NFPA oxidizer classification that is not higher than class 2, i.e., the mixture has a class 1 or class 2 NFPA classification.

The term "calcium hypochlorite" means calcium hypochlorite having an unspecified amount of bound water or water of hydration, and includes hydrated calcium hypochlorite and dry calcium hypochlorite. The term "calcium hypochlorite" includes calcium hypochlorite that also contains inorganic salts, oxides and/or hydroxides that are incorporated into the calcium hypochlorite incidental to the calcium hypochlorite manufacturing process.

The term "hydrated calcium hypochlorite" means calcium hypochlorite having from 5.5 to 16 weight percent water, e.g., as bound water or as water of hydration. See, Calcium Hypochlorite, Hydrated (UN #2880) in 49 CFR 172.101, Hazardous Materials Table.

The term "dry calcium hypochlorite" means calcium hypochlorite having less than 5.5 weight percent water, e.g., as bound water or as water of hydration. See, calcium hypochlorite, dry (UN #1748) in 49 CFR 172.101.

The terms "halogen-containing sanitizer material", "sanitizer material", or terms of like import means a halogen-containing material that forms hypohalous acid or hypohalite anion in an aqueous medium. Non-limiting representative examples of such materials include the hypochlorites, such as lithium hypochlorite and calcium hypochlorite, chlorinated isocyanuric acids, such as dichloroisocyanuric acid and its corresponding sodium and potassium salts, trichloroisocyanuric acid, the chlorinated and brominated hydantoins, e.g., 1,3-dibromo-5,5-dimethylhydantoin, the N-halo-2-oxazolidinones, e.g., 3-chloro-4,4-dimethyl-2-oxazolidinone, and N,N'-dihalo-2-imidazolidinones, e.g., 1,3-dichloro-4,4,5,5-tetramethyl-2-imidazolidinone.

The term "major amount" means an amount of at least 50 weight percent.

The term "minor amount" means an amount of less than 50 weight percent.

The terms "mixture", "admixture", "blend" or terms of like import, as used for example in connection with a described mixture of calcium hypochlorite and calcium oxide-modified boric acid means that the mixture, admixture or blend comprises a physical intermingling of the described materials. The physical intermingling includes, but is not limited to, particulate calcium hypochlorite coated (partially or completely) with the calcium oxide-modified boric acid. The terms "mixture", "admixture", "blend" or terms of like import is intended to include formed articles, e.g., tablets or other shaped forms, prepared from such mixtures, admixtures or blends of calcium hypochlorite and calcium oxide-modified boric acid.

The term "solid" means a physical state other than liquid or gaseous.

As previously mentioned, the present invention provides a composition comprising (a) a major amount of solid halogen containing sanitizer material and (b) a minor amount of calcium oxide-modified particulate boric acid, which is present in said composition in amounts sufficient to enable the composition to be classified as a class 1 or class 2 NFPA oxidizer.

Non-limiting examples of solid halogen-containing sanitizer material include alkali metal hypochlorites, such as lithium hypochlorite; alkaline earth metal hypochlorites, such as calcium hypochlorite; halogenated hydantoins, such as the chlorinated and brominated hydantoins, e.g., 1,3-dibromo-5,5-dimethylhydantoin; chlorinated isocyanuric acid and its alkali metal derivatives, e.g., trichloroisocyanuric acid, dichloroisocyanuric acid, and sodium and potassium dichloro-s-triazinetrione; the N-halo-2-oxazolidinones, such as 3-chloro-4,4-dimethyl-2-oxazolidinone; and N,N'-dihalo-2-imidazolidinones, such as 1,3-dichloro-4,4,5,5-tetramethyl-2-imidazolidinone.

Calcium hypochlorite [CAS 7778-54-3] is a known and commercially available material. Commercial grades of calcium hypochlorite typically contain at least 39, e.g., at least 45 weight percent FAC. Some commercial grades of calcium hypochlorite contain at least 50 or 55 weight percent FAC, and often contain at least 60 weight percent FAC, e.g., between 60 or 65 and 80 percent FAC. In a non-limiting embodiment of the present invention, calcium hypochlorite that may be used to prepare the herein described compositions can contain between 39 and 80 weight percent FAC. The calcium hypochlorite also may contain between 45 and 80, such as 50 and 80, or 65 and 80, or 65 and 76 weight percent of FAC. Calcium hypochlorite used to prepare the compositions of the present invention can contain an amount of FAC that is within a range that may vary between any of the recited values.

Chemically, the remainder of the components of commercially available grades of calcium hypochlorite typically comprise varying amounts of water, and varying small amounts of by-product calcium compounds and alkali metal salts incorporated into the calcium hypochlorite product as an incident to the manufacturing process. Such inorganic salts include, but are not limited to, sodium chloride, calcium chloride, calcium hydroxide, calcium carbonate and calcium chlorate.

Water generally comprises between 5.5 and 16 percent by weight of current commercially available high strength hydrated calcium hypochlorite, although amounts of less than 5.5 weight percent may be present in dry calcium hypochlorite, e.g., 1 to 2 weight percent. Alternatively, water can comprise 12 percent by weight or less, e.g., 10 percent by weight or less and often 8.5 percent by weight or less, of commercially available calcium hypochlorite. The amount of water present in commercial grades of hydrated high strength calcium hypochlorite may range between 5.5 and 10 percent, such as between 5.5 and 8.5, e.g., between 6.5 and 7.5 percent, by weight of the calcium hypochlorite material. The amount of water that is present in calcium hypochlorite may vary between any combination of the specified values, inclusive of the recited values. Commercially available grades of calcium hypochlorite, e.g., such as the aforedescribed high strength hydrated calcium hypochlorite materials, can be used to prepare the calcium hypochlorite compositions of the present invention. Calcium hypochlorite is a hydrophilic material and dissolves in water. It has a reported solubility in water at 25° C. of 21.4 percent.

The particle size and particle size distribution of current commercially available particulate calcium hypochlorite can vary, e.g., it can vary from a powder to a granular material. As a general guideline, commercially available granular calcium hypochlorite has a principal size distribution between 100 and 6 mesh, as measured by the American Standard Test Method E11 Alternative Sieve Designation (ASTM E11 ASD); namely, the particles vary in size principally between 0.15 millimeters (mm) (0.006 inches) and 3.35 mm (0.13 inches). In a non-limiting embodiment, particulate calcium hypochlorite may have a principal particle size distribution between 100 mesh (0.15 mm) and 10 mesh (1.8 mm), e.g., between 45 mesh (0.33 mm) and 14 mesh (1.17 mm), based on ASTM E11 ASD. Further, when solid formed articles of the calcium hypochlorite compositions of the present invention are prepared, one skilled in the art will typically select a particle size distribution for the calcium hypochlorite that is amenable to be formed, e.g., compressed, into the desired solid formed article, e.g., a tablet. A non-limiting example of commercially available granular calcium hypochlorite that can be used to prepare calcium hypochlorite compositions of the present invention is available from PPG Industries, Inc. under the trademark PITTCLOR®. Other non-limiting examples of granular calcium hypochlorite that can be used include calcium hypochlorite sold under the brand names, INDU-CLOR® 70, ZAPPIT® 73 and LESLIE'S® Power Powder® Pro.

Calcium hypochlorite, as described herein, is typically present in the compositions of the present invention in a major amount. In a non-limiting embodiment, the calcium hypochlorite is present in the compositions of the present invention in an amount of at least 75 weight percent, e.g., at least 80 weight percent. The calcium hypochlorite may be present in the compositions of the present invention in amounts of at least 85 weight percent, such as at least 90 weight percent, e.g., 95 to 99.5 weight percent. The calcium hypochlorite may be present in the compositions of the present invention in amounts that range between any of the previously stated values, including the recited values.

Alternatively, the calcium hypochlorite may be present in the compositions of the present invention in amounts sufficient to provide at least 39 percent by weight FAC, such as at least 45 percent by weight FAC, e.g., 50 to 65 percent by weight FAC, based on the total weight of the composition. In a further non-limiting embodiment, the calcium hypochlorite is present in the composition in amounts that provide less than approximately 80 percent by weight FAC, e.g., less than 76 percent by weight FAC, based on the total weight of the composition. Compositions prepared in accordance with the present invention may have present therein calcium hypochlorite in an amount sufficient to provide an FAC content ranging between any of those stated values, inclusive of the recited values, e.g., between 65 and 76 percent by weight FAC.

Lithium hypochlorite is available commercially as a free-flowing, white granular product containing about 35 percent available chlorine. Major by-products found in lithium hypochlorite include sodium chloride and sodium or potassium sulfate. Minor amounts of lithium chloride, lithium chlorate, lithium hydroxide and lithium carbonate are also found in the product. Water typically comprises about 7 percent by weight of the lithium hypochlorite article of commerce. Granular lithium hypochlorite generally has a particle size between −10 (1.98 millimeters) and +70 (0.21 millimeters) US Sieve series.

Chlorinated isocyanurates are a further example of a solid halogen-containing material that can be used to prepare the compositions of the present invention. The two most commonly used chlorinated isocyanurates are dichloroisocyanuric acid and its sodium and potassium salts. Dichloroisocyanuric acid is commonly available as the sodium salt in the form of a white granular substance having from 62 to 70 percent available chlorine. It is also sold in the dihydrate form. Trichloroisocyanuric acid (often referred to as "Trichlor" for brevity) is a white granular powder or granule which is commercially available containing about 90 percent available chlorine. It is often formulated with cyanuric acid in amounts of 1 part cyanuric acid to from 2 to 4 parts of Trichlor.

A further group of solid halogen-containing disinfecting materials that can be used to prepare the compositions of the present invention are halogenated, e.g., brominated and chlorinated, dimethyl hydantoins, such as 1,3-dibromo-5,5-dimethylhydantoin, 1,3-dichloro-5,5-dimethylhydantoin and 1-bromo-3-chloro-5,5-dimethylhydantoin. 1,3-dibromo-5,5-dimethylhydantoin is available commercially as a free-flowing cream colored powder containing about 55 percent active bromine. 1,3-dichloro-5,5-dimethylhydantoin is commercially available as a white powder containing approximately 36 percent active chlorine. These hydantoins may be prepared respectively by brominating or chlorinating dimethylhydantoin. 1-bromo-3-chloro-5,5-dimethyhydantoin is available commercially as a free-flowing white powder containing approximately 33 percent active bromine and 14 percent active chlorine, It can be prepared by the sequential chlorination and bromination of dimethylhydantoin.

The N-halo-2-oxazolidinones that can be used to prepare compositions of the present invention can be represented by the following general formula (I):

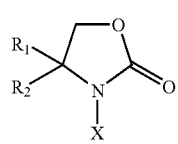

wherein X is chlorine or bromine, $R_1$ is $C_1$-$C_4$ alkyl, such as methyl, ethyl, propyl, isopropyl, butyl, isobutyl, and secondary butyl, and $R_2$ is chosen from $R_1$, hydroxy, hydroxymethyl, $C_1$-$C_4$ alkoxy, such as methoxy, ethoxy, propoxy, isopropoxy and butoxy, e.g., n-butoxy, isobutoxy and secondary butoxy, and substituted phenyl (-Ph-R), particularly para-substituted phenyl, wherein Ph is bivalent substituted phenyl (phenylene) and said phenyl substituents, R, are chosen from $C_1$-$C_4$ alkyl, e.g., methyl and ethyl. Typically, $R_1$ and $R_2$ are the same, e.g., methyl.

Examples of N-halo-2-oxazolidinones include, but are not limited to: 3-chloro-4,4-dimethyl-2-oxazolidinone, 3-chloro-4,4-diethyl-2-oxazolidinone, 3-chloro-4-methyl-4-ethyl-2-oxazolidinone, 3-chloro-4-methyl-4-hydroxy-2-oxazolidinone, 3-chloro-4-methyl-4-methoxy-2-oxazolidinone, 3-chloro-4-methyl-4-hydroxymethyl-2-oxazolidinone, and 3-chloro-4-methyl-4-p-methylphenyl-2-oxazolidinone.

N,N'-dihalo-2-imidazolidinones that can be used to prepare the compositions of the present invention can be represented by the following general formula (II):

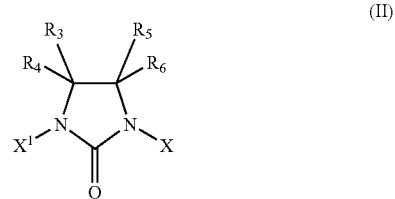

wherein X and $X^1$ are each halogen chosen from chlorine and bromine, $R_3$, $R_4$, $R_5$ and $R_6$ are each chosen from hydrogen, $C_1$-$C_4$ alkyl, $C_1$-$C_4$ alkoxy, hydroxy and substituted phenyl, e.g., para-substituted phenyl. The phenyl substituents can be chosen from $C_1$-$C_4$ alkyl, $C_1$-$C_4$ alkoxy and hydroxy; provided that not more than one of the substituents $R_3$-$R_6$ is hydrogen.

Non-limiting examples of N,N'-dihalo-2-imidazolidinones include: 1-bromo-3-chloro-4,4,5,5-tetramethyl-2-imidazolidinone, 1,3-dichloro-4,5,5-trimethyl-2-imidazolidinone, 1,3-dichloro-4-methoxy-4,5,5-trimethyl-2-imidazolidinone, 1,3-dibromo-4,4,5,5-tetramethyl-2-imidazolidinone, 1,3-dichloro-4,4,5,5-tetramethyl-2-imidazolidinone, 1,3-dichloro-4-hydroxy-4,5,5-trimethyl-2-imidazolidinone, 1,3-dichloro-4-ethyl-4,5,5-trimethyl-2-imidazolidinone, 1,3-dichloro-4,4-diethyl-5,5-dimethyl-2-imidazolidinone, and 1,3-dichloro-4,4,5,5-tetraethyl-2-imidazolidinone.

In a non-limiting embodiment of the present invention, compositions comprising a mixture of (a) a major amount of solid halogen-containing sanitizer material, e.g., calcium hypochlorite, and (b) a minor amount of calcium oxide-modified particulate boric acid are formulated so that the resulting mixture is not classified as a US DOT Packing Group I or Packing Group II Division 5.1 oxidizer material, but is classified as a Packing Group III Division 5.1 oxidizer or a non-Division 5.1 oxidizer. In accordance with the NFPA classifications, such compositions are not categorized as a NFPA class 4 or class 3 oxidizer material, but as a NFPA class 1 or 2 oxidizer material.

In accordance with regulations of the US DOT, 49 CFR §173.127(a), an "oxidizer" (Division 5.1) is defined as a material that may, generally by yielding oxygen, cause or enhance the combustion of other materials. A solid material is classified as a Division 5.1 material if, when it is tested in accordance with the UN Manual of Tests and Criteria, it has a mean burning time that is less than or equal to the burning time of a 3:7 potassium bromate-cellulose mixture [49 CFR §173.127(a)(1)].

Solid Division 5.1 materials are assigned packing group classifications using the following criteria [49 CFR §173.127 (b)]:

(i) Packing Group I is the sub-classification of any material which, in the 4:1 or 1:1 sample to cellulose ratio (by mass) tested, exhibits a mean burning time less than the mean burning time of a 3:2 mixture, by mass, of potassium bromate and cellulose.

(ii) Packing Group II is the sub-classification of any material which, in the 4:1 or 1:1 sample to cellulose ratio (by mass) tested, exhibits a mean burning time less than the mean burning time of a 2:3 mixture, by mass, of potassium bromate and cellulose, and the criteria for Packing Group I are not met.

(iii) Packing Group III is the sub-classification of any material which, in the 4:1 or 1:1 sample to cellulose ratio (by mass) tested, exhibits a mean burning time less than the mean burning time of a 3:7 mixture, by mass, of potassium bromate and cellulose, and the criteria for Packing Groups I and II are not met.

A non-Division 5.1 material is a material which, in the 4:1 or 1:1 sample to cellulose ratio (by mass) tested, does not ignite and burn, or exhibits a mean burning time greater than that of a 3:7 mixture, by mass, of potassium bromate and cellulose.

Oxidizer classifications in accordance with National Fire Protection Association are described as follows:

(i) Class 1—An oxidizer that meets the definition of an oxidizer and does not moderately increase the burning rate of combustible materials with which it comes into contact. An example of a class I oxidizer is lithium hypochlorite.

(ii) Class 2—An oxidizer that will cause a moderate increase in the burning rate of combustible materials with which it comes into contact. An example of a class 2 oxidizer is calcium hypochlorite containing less than 50 percent FAC.

(iii) Class 3—An oxidizer that will cause a severe increase in the burning rate of combustible materials with which it comes into contact or that will undergo vigorous self-sustained decomposition due to contamination or exposure to heat. An example of a class 3 oxidizer is calcium hypochlorite having greater than 50 percent FAC.

(iv) Class 4—An oxidizer that can undergo an explosive reaction due to contamination or exposure to thermal or physical shock. In addition, the oxidizer will cause a severe increase in the burning rate of combustible materials with which it comes into contact.

In a non-limiting embodiment of the present invention, solid halogen-containing sanitizer, e.g., calcium hypochlorite, is present in the described compositions in amounts at least sufficient to provide a FAHal content, e.g., FAC, that would result in such compositions being classified as a Packing Group I or II oxidizer (by DOT regulations) or a class 3 or class 4 oxidizer (by NFPA regulations) if the calcium oxide-modified particulate boric acid was not present in the composition.

In the case of calcium hypochlorite compositions of the present invention, the calcium hypochlorite is present in the described compositions in amounts sufficient to provide at least 39 percent by weight FAC, more usually at least 45 percent by weight FAC, e.g., from 50 to 65 percent by weight FAC, based on the total composition weight. In a further embodiment, the calcium hypochlorite is present in the composition in amounts that provide less than approximately 80 percent or 76 percent FAC by weight, e.g., less than 65 percent by weight FAC, based on total composition weight. Calcium hypochlorite compositions prepared in accordance with the present invention can have present therein calcium hypochlorite in an amount sufficient to provide an FAC content ranging between any of these stated values, inclusive of the recited values.

In a non-limiting embodiment of the present invention, solid halogen-containing sanitizer is present in the described compositions in a major amount. The solid halogen-containing sanitizer, e.g., calcium hypochlorite, may also be present in the described compositions in amounts of from 70 to 90 weight percent, e.g., from 80 to 85 weight percent.

Boric acid (orthoboric acid) [CAS 10043-35-3] is commercially available in at least three grades of granular and powdered form. Calcium oxide is also available commercially. In accordance with a non-limiting embodiment of the present invention, calcium oxide-modified particulate boric acid is prepared by heating a mixture of particulate calcium oxide and particulate boric acid in a suitable vessel under conditions that results in the calcium oxide adhering to the surface of the particulate boric acid.

In a non-limiting embodiment, the mixture of particulate calcium oxide and particulate boric acid is heated at temperatures within the range of from 60° C. to 140° C. In an alternate embodiment, the mixture is heated at a temperature of at least 90° C., such as at temperatures of from 90° C. to 130° C., or 100 to 120° C., for a period of time sufficient to allow particles of calcium oxide to adhere, e.g., stick, to the surfaces of the boric acid particles. Such time periods can range from 0.5 to 20 hours, e.g., from 1 to 16 hours, such as from 2 to 8 hours. In a contemplated embodiment, vacuum is applied to the vessel containing the mixture of calcium oxide and boric acid during the heating period to assist in the removal of water vapor from the mixture. The vacuum applied need only be that required to enhance the removal of water during the heating period, e.g., a slight vacuum. Typically, the length of time and temperature at which the calcium oxide/boric acid mixture is heated is chosen so that the calcium oxide-modified boric acid product is substantially free of calcium borate by-products. For example, in a non-limiting embodiment analysis of the calcium oxide-modified boric acid product indicates that the product is substantially free of calcium borate salts.

The amount of particulate calcium oxide that is blended with the particulate boric acid to prepare the calcium oxide-modified boric acid can vary widely. In a non-limiting embodiment of the present invention, one part of calcium oxide is blended with from 1.5 to 8 parts of boric acid (by weight). In other examples, one part of calcium oxide is blended with from 1.5 to from 3 to 5, e.g. 4, parts (by weight) of boric acid. Scanning electron microscopic images of calcium oxide-modified boric acid prepared from such blends show that at least a portion of the surface of the treated (heated with calcium oxide) boric acid particles are covered with individual specs of smaller particles of calcium oxide rather than a continuous layer of calcium oxide. However, it is contemplated that in an alternate embodiment the calcium oxide forms an at least partially continuous coating on the surfaces of the boric acid particles.

The amount of calcium oxide-modified particulate boric acid blended with the solid halogen-containing sanitizer, e.g., calcium hypochlorite, can vary. Such amounts will depend in part on the available halogen content of the sanitizer material used and the level of oxidizer classification that is desired. In a non-limiting embodiment, the amount of calcium oxide-modified boric acid blended with the halogen-containing sanitizer is a minor amount. In an alternate example, the amount of calcium oxide-modified boric acid that is mixed with the solid sanitizer material, e.g., calcium hypochlorite, is that amount that is sufficient for the resulting blend to have at least a class 2 NFPA oxidizer classification, i.e., a class 1 or class 2 NFPA oxidizer classification. In terms of US DOT classifications, the amount of calcium oxide modified particulate boric acid that is mixed with the solid sanitizer material, e.g., calcium hypochlorite, is that amount that is sufficient for the resulting blend to have a Packing Group III classification or a Non-Division 5.1 oxidizer status.

In a non-limiting embodiment, the amount of calcium oxide-modified particulate boric acid added to the solid halogen-containing sanitizer, e.g., calcium hypochlorite, can vary from 10 to 30 weight percent, such as, from 15 to 25 weight percent, based on the total weight of the composition. Amounts less than 10 weight percent are contemplated. Similarly, amounts greater than 30 weight percent also are contemplated, however a cost/benefit analysis of such higher amounts will determine whether use of such larger quantities is commercially and economically justified.

Compositions of the present invention comprising halogen-containing sanitizing materials and calcium oxide-modified particulate boric acid, e.g., blends of calcium hypochlorite and calcium oxide-modified boric acid, can be prepared readily by blending in a suitable mixing vessel the desired amounts of particulate halogen-containing material, such as calcium hypochlorite, e.g., granular calcium hypochlorite, and particulate, e.g., powdery or granular calcium oxide-modified boric acid, until the blend is substantially homogeneous. The resulting blends are removed from the mixing vessel and used, packaged for sale or formed into solid shaped articles, e.g., tablets.

The compositions of the present invention may also contain additives, e.g., adjuvants, that do not deleteriously affect the sanitizing effectiveness of the composition. In a non-limiting embodiment, the adjuvant(s) also does not cause the composition to be classified as a Division 5.1 oxidizer or as a class 3 NFPA oxidizer. For example, when the compositions of the present invention are formed into solid shaped articles, e.g., tablets, adjuvant additives that may be present include, but are not limited to, conventional binders and buffering agents. Other additives that may be present when the compositions are in either tablet or granular form include, but are not limited to, chemically compatible scale inhibitors and colorant-containing inorganic salts, such as those described in U.S. Pat. No. 5,049,385, at column 5, line 62 through column 7, line 8, which disclosure is incorporated herein by reference.

Use of calcium oxide-modified particulate boric acid in combination with calcium hypochlorite permits the preparation of calcium hypochlorite compositions having an available chlorine content of at least 39 percent, e.g., at least 45 or 50 percent, which compositions can be classified as Packing Group III oxidizers or as non-Division 5.1 oxidizers, or as NFPA class 2 or class 1 oxidizers. Further, calcium hypochlorite compositions that comprise calcium oxide-modified particulate boric acid and added inert inorganic solid diluent(s), such as anhydrous inorganic salts, are contemplated herein. Typically, the inert inorganic solid diluents are pH neutral.

Non-limiting examples of inert, inorganic anhydrous solid diluent materials include sodium chloride, potassium chloride, lithium chloride, calcium chloride, calcium oxide, calcium hydroxide, magnesium hydroxide, aluminum hydroxide, sodium sulfate, magnesium sulfate, magnesium silicate (talc) and mixtures of such inorganic inert materials. By inert is meant that the inorganic material does not affect substantially the shelf life of the calcium hypochlorite, or the SADT (self accelerating decomposition temperature) of the calcium hypochlorite. In a non-limiting embodiment, calcium hypochlorite compositions comprising calcium oxide-modified boric acid and solid inorganic, inert diluent materials, e.g., pH neutral salts, may be formulated to contain from 10 to 30, e.g., 15 to 20, weight percent of calcium oxide-modified boric acid, from 8 to 25, e.g., 10 to 20, weight percent of the inorganic inert diluent material, and sufficient calcium hypochlorite so that the FAC content of the composition is at least 39 percent, alternatively at least 45 percent. In another example, the FAC content is at least 50 percent, e.g., at least 55 percent.

Adjuvant additives, including the added inert inorganic diluent anhydrous materials, added to the solid halogen-containing sanitizing material, e.g., calcium hypochlorite/calcium oxide modified-boric acid compositions of the present invention are generally present in amounts, for example, ranging from 0.001 percent to 15 percent by weight, alternatively from 0.01 percent to 12 percent by weight, e.g., from 0.1 to 5 percent by weight, based on the total weight of the composition. The amount of each of such additives that can be added to the compositions of the present invention can vary between any of the aforestated values, inclusive of the recited values. For example, non-limiting examples of such additives and their amounts include, but are not limited to, sodium tripolyphosphate, which in one non-limiting embodiment can be present in amounts of from 1 to 5, e.g., 3 weight percent; and added inert salts, e.g., sodium chloride, which in one non-limiting embodiment can be present in amounts of from 8 to 15, e.g., 10 to 12, weight percent.

In a non-limiting embodiment of the present invention, hydrated lime (calcium hydroxide), magnesium hydroxide, aluminum hydroxide and/or magnesium silicate can be added to a calcium hypochlorite composition. When the calcium hypochlorite compositions of the present invention are used for the treatment of residential waste water, hydrated lime is particularly desirable as an additive. In such applications, the amount of added hydrated line may in one non-limiting embodiment range from 0.5 to 5 weight percent, such as from 1 to 2.5 weight percent, based on the total weight of the composition.

In a further example of the present invention, a particulate, inert hygroscopic material can be added to the sanitizing, e.g., calcium hypochlorite, composition in relatively small amounts to capture small amounts of free water that is absorbed by the composition from the surrounding environment, e.g., due to high humidity. The inert hygroscopic material can be added to the sanitizing composition to absorb free water that may be present in the original solid halogen-containing sanitizing material, e.g., calcium hypochlorite, or to absorb water that is liberated from components of the sanitizing composition during storage. Non-limiting examples of inert, hygroscopic materials are finely divided amorphous silica, e.g., precipitated silica, silica gel or pyrogenic (fumed) silica. In one embodiment, the hygroscopic material is present in amounts of less than 5 weight percent, based on the total weight of the sanitizing, e.g., calcium hypochlorite, composition.

In another example of the present invention, at least one separate desiccant package, e.g., a canister containing a desiccant, is added to a container holding the sanitizing compositions, e.g., calcium hypochlorite compositions of the present invention. Such sanitizing compositions can, for example, be in particulate form, e.g., granular material, or in the form of shaped articles, e.g., tablets. The desiccant package is adapted to absorb moisture present in the container, which moisture may be that present, for example, under conditions of high humidity, thereby to limit exposure of the sanitizing composition's exposure to such humidity. The container is generally fabricated from a material or materials that are chemically resistant to compositions comprising halogen-containing sanitizing material, e.g., calcium hypochlorite compositions, that are described herein and that satisfy transportation regulations, e.g., U.S. Department of Transportation regulations. The container can be sized to accommodate anywhere from 1 to 400 pounds of the sanitizing material. Non-limiting examples of containers or packages include pouches, such as a single application package, boxes, gallon pails, drums, e.g., drums that contain 50, 100 and 400 pounds of material, etc, of the halogen-containing sanitizing composition, e.g., a calcium hypochlorite/calcium oxide-modified boric acid composition The compositions of the present invention, usually in the form of granules, pellets or tablets, can be added directly to an aqueous medium to be treated, e.g., sanitized, or can be added to any suitable chlorination unit or device, which is used to prepare an aqueous solution of the halogen-containing sanitizer material, e.g., calcium hypochlorite, which solution in turn is used to sanitize an aqueous body of water, e.g., a swimming pool, hot tub or spa. Non-limiting examples of suitable chlorination units are those described in FIG. 1 of U.S. Pat. No. 5,384,102, FIG. 1 of U.S. Pat. No. 5,427,748 and FIG. 1 of U.S. Pat. No. 6,298,871 B1, which disclosures are incorporated herein by reference.

An aqueous stream or body of water that has been sanitized by contact with the compositions of the present invention, or with aqueous solutions prepared from such compositions, can be used in various applications, e.g., standing and recirculating water systems, such as cooling towers, evaporative condensers, air washers, swimming pools, hot tubs, spas, etc, for the treatment of residential waster water and for the preparation of hypochlorite ion-containing aqueous solutions used for sanitizing food and the surfaces and equipment used in the processing of food products (raw and processed). When used to sanitize the surface of an article, the hypochlorite ion-containing aqueous solution can be applied to food and such surfaces by any appropriate method. Non-limiting examples of such methods include spraying; wiping with soaked rags; curtain or waterfall applications; and soaking by immersion.

Compositions of the present invention may be formed into solid shaped articles, including but not limited to, tablets, bricks, briquettes, pellets, etc, by conventional size enlargement equipment. Examples of such equipment include, but are not limited to, molding presses, tableting presses, roll-type presses, pellet mills and screw extruders. In a non-limiting embodiment, the solid shaped article can have a mass of between 1 gram and 350 grams or more, e.g., between 7 and 300 grams. The size of the solid shaped article may vary widely and is determined typically by the intended application, such as the internal dimensions and operating parameters of the chlorination unit in which the solid shaped article is to be used, and/or conventional commercial handling and packaging units.

In the case of a solid shaped article that is formed in the shape of a tablet having a mass of, for example, from 140 to 350 grams, the diameter of the tablet in one contemplated embodiment can be between 6.7 centimeters (cm) (2.625 inches) and 8.9 cm (3.5 inches), e.g., between 7.9 cm (3.125 inches) and 8.3 cm (3.25 inches), and have a thickness of from 2.5 cm (1 inch) to 5.1 cm (2 inches), e.g., 3.2 cm (1.25 inches). The dimensions of such tablets can vary between any of the aforestated recited values.

In a non-limiting embodiment granular calcium hypochlorite having a size distribution predominantly between 45 mesh and 10 mesh ASTM E11 ASD, e.g., the granules are principally between on average 0.36 mm (0.014 inches) and 2.00 mm (0.08 inches), is used to produce solid shaped articles such as tablets. Particles smaller than 50 mesh ASTM E11 ASD, e.g., 0.30 mm (0.012 inches), that are present in the granular calcium hypochlorite generally represent a minor percentage, usually less than 2 percent, of the material charged to a size enlargement device.

The present invention is more particularly described in the examples that follow, which are intended to be illustrative only, since numerous modifications and variations therein will be apparent to those skilled in the art. Unless otherwise specified, all parts and percentages are by weight.

The test for oxidizing materials described in the United Nations Manual of Tests and Criteria was used to determine the oxidizer characteristics for the samples tested in the Examples. Test method details are found in Section 34 of the aforementioned Manual ("Recommendations on the Transport of Dangerous Goods; Manual of Tests and Criteria"), (Revision 3), which is titled "Classification Procedures, Test Methods and Criteria Relating to Oxidizing Substances of Division 5.1". In the test, the relative burning rate of various materials (calcium hypochlorite and blends of calcium hypochlorite with calcium oxide modified boric acid in the present case) are compared to a reference material (a blend of potassium bromate and cellulose in a weight ratio of 3:7). On the basis of this test, the test material can be defined as an oxidizer or a non-oxidizer, and if it is an oxidizer, it can be further classified into one of three Packing Groups, as defined by the aforesaid regulations of the US DOT.

The burn test procedure can be summarized as follows. A 30 cm±1 cm length of nickel-chromium wire having a diameter of 0.6±0.05 mm and a resistivity of 6.0±0.5 ohms/meter is laid in a serpentine fashion over a circular area of 38.5 square centimeters ($cm^2$) on a 15 cm×15 cm×0.6 cm cement tile (plate or slab) having a thermal conductivity (at 0° C.) of 0.23 $W.m^{-1}.K^{-1}$. The wire is held in place by two electrically conductive screw-type contacts located outside of the 38.5 $cm^2$ circular area. A homogeneously mixed reference sample (30 grains) is prepared from potassium bromate (pre-dried at 65° C. for a minimum of 12 hours) and cellulose (pre-dried at 115° C. for a minimum of 4 hours to contain less than 0.5 percent water by dry weight) in a weight ratio of 3:7 respectively. The potassium bromate and cellulose are mixed together by hand in a small glass beaker using a spatula. The potassium bromate [Fisher Scientific (catalog number P207-250)] has a purity of 99 percent by weight. The cellulose is in the form of a medium fiber powder, which has a Whatman® advanced ion exchange cellulose designation of CF-11 [Fisher Scientific (catalog number 05-713-004)], and is stored in a desiccator.

To a 60° conical glass funnel, having a large end diameter of 70 mm and a sealed small end, is added 30 grams of the sample to be tested. The 38.5 $cm^2$ circular area of the cement tile having the nickel-chromium wire affixed to it, is placed over the 70 mm diameter opening of the filled funnel. The cement tile and funnel are together flipped over such that the funnel sits in an inverted fashion upon the block. The funnel is lifted away leaving a truncated conical pile of the sample over the nickel-chromium wire to which is applied an alternating current sufficient to provide 150±7 watts of power. Current is applied to the wire throughout the duration of the test or for a maximum of three minutes if no burning of the sample is observed.

Burn times are taken from the moment power is applied to the wire until the sample is observed to stop burning. The burn time for the potassium bromate/cellulose reference sample is taken from the average of five separate burn tests, which are performed under ambient atmospheric conditions. To minimize subjective influences on the results of the burn tests, a separate set of reference sample burn times are generated every time a set of test blends is evaluated. The burn time for the potassium bromate-cellulose (3:7) reference samples averaged 83 seconds. Test materials having a burn time of greater than 83 seconds are considered to be non-oxidizers based on the UN Division 5.1 Oxidizer Classification Test.

EXAMPLE 1

Boric Acid (15 parts) obtained from Fischer Scientific (+8 mesh, Alfa-Aesar) was blended with 10 parts of calcium oxide powder (Fischer Scientific-C117 Certified) in a glass container. The blend was heated at 100° C. for 16 hours. 75 parts of granular calcium hypochlorite (ZAPPIT® 73 Grade, PPG Industries, Inc.) having a particle size ranging mainly from 60 US Mesh (0.26 mm) to 18 US Mesh (1.03 mm) (ASTM E11 ASD), a FAC content of approximately 73 percent and approximately 6.8 percent water (both based on the total weight) was mixed with 25 parts of the boric acid-calcium oxide blend (prepared as described) in a beaker by hand with a stainless steel spatula until the mixture was observed visually to be as homogenous as the mixture would allow.

The foregoing mixture was blended with cellulose (pre-dried at 105 C for 4 hours, and stored in a desiccator) in a weight ratio of 4:1 (mixture:cellulose) and the burn time of the mixture determined in accordance with the burn test procedure previously described (Section 34 of the UN Manual of Test and Criteria). The burn time result is tabulated in Table 1. The reported burn time is the average of three burn tests.

EXAMPLES 2-6

The procedures and test methods described in Example 1 were repeated for Examples 2 through 6 except that the amounts of boric acid and calcium oxide were changed, as indicated in Table 1. Results of the burn times for Examples 2-6 are tabulated in Table 1. The reported burn times in Table 1 are the average of three burn tests for each line in the table.

COMPARATIVE EXAMPLE (CE)

The burn test described in Example 1 was repeated for calcium hypochlorite alone (without any calcium oxide-modified boric acid). The calcium hypochlorite used was the same as that used in Examples 1-6. Results are tabulated in Table 1.

TABLE 1

| Example # | % Ca(OCl)$_2$[a] | % CaO | % Boric acid(BA) | Weight ratio BA/CaO | Burn time, sec | UN/DOT Pk. Gr.[b] |
|---|---|---|---|---|---|---|
| CE | 100 | — | — | — | 11 | II |
| 1 | 75 | 10 | 15 | 1.5 | 46 | III |
| 2 | 75 | 8 | 17 | 2.1 | 53 | III |
| 3 | 75 | 7 | 18 | 2.6 | 73 | III |
| 4 | 75 | 6 | 19 | 3.2 | 101 | Non-Ox |
| 5 | 75 | 5 | 20 | 4.0 | 121 | Non-Ox |
| 6 | 75 | 3 | 22 | 7.3 | 120 | Non-Ox |

[a]Calcium hypochlorite, 71% assay.
[b]Packing Group Classification

The results of Table 1 demonstrate that blending calcium oxide-modified boric acid with calcium hypochlorite can increase the burn time of the blend and provide a material that has a UN/DOT Packing Group III classification or a material that is classified as a non-oxidizer (Non-Ox).

The present invention has been described with reference to specific details of particular embodiments thereof. It is not intended that such details be regarded as limitations upon the scope of the invention except insofar as and to the extent that they are included in the accompanying claims.

What is claimed is:

1. A composition comprising a mixture of (a) a major amount of solid halogen-containing sanitizer material and (b) a minor amount of calcium oxide-modified particulate boric acid, the amount of said calcium oxide-modified boric acid in said composition being sufficient to enable the composition to be classified as a class 1 or class 2 NFPA oxidizer.

2. The composition of claim 1 wherein the solid halogen-containing sanitizer is chosen from lithium hypochlorite, alkaline earth metal hypochlorites, halogenated hydantoins, chlorinated isocyanuric acid, alkali metal derivatives of chlorinated isocyanuric acid, N-halo-2-oxazolidinones or N,N'-dihalo-2-imidazolidinones.

3. The composition of claim 2 wherein the solid halogen-containing sanitizer is chosen from calcium hypochlorite, 1,3-dibromo-5,5-dimethylhydantoin, trichloroisocyanuric acid, dichloroisocyanuric acid, sodium dichloro-s-triazinetrione or potassium dichloro-s-triazinetrione.

4. The composition of claim 3 wherein the calcium oxide-modified particulate boric acid is present in the composition in an amount of from 10 to 30 weight percent, based on the amount of solid halogen-containing sanitizer.

5. The composition of claim 4 wherein the calcium-oxide-modified particulate boric acid comprises 1 part of calcium oxide to from 1.5 to 8 parts of boric acid.

6. A composition comprising a mixture of (a) from 70 to 90 weight percent calcium hypochlorite and (b) from 30 to 10 weight percent of calcium oxide-modified particulate boric acid, the amount of said calcium oxide modified particulate boric acid in said composition being sufficient to enable the composition to be classified as a class 1 or class 2 NFPA oxidizer.

7. The composition of claim 6 wherein the available chlorine content of the calcium hypochlorite is at least 45%.

8. The composition of claim 7 wherein the calcium oxide-modified particulate boric acid comprises 1 part of calcium oxide to from 1.5 to 8 parts of boric acid.

9. The composition of claim 8 wherein the calcium oxide-modified particulate boric acid is present in the composition in an amount of from 15 to 25 weight percent, based on the amount of calcium hypochlorite, and the calcium oxide-modified particulate boric acid comprises 1 part of calcium oxide to from 1.5 to 4 parts of boric acid.

10. The composition of claim 1 wherein the calcium oxide modified particulate boric acid is prepared by blending calcium oxide and boric acid in a ratio of one part of calcium oxide to from 1.5 to 8 parts of boric acid, and heating the blend at temperatures of at least 90° C. for from 0.5 to 20 hours.

11. The composition of claim 6 wherein the calcium oxide modified particulate boric acid is prepared by blending calcium oxide and boric acid in a ratio of one part of calcium oxide to from 1.5 to 4 parts of boric acid, and heating the blend at temperatures of from 90° C. to 130° C. for from 1 to 16 hours.

* * * * *